United States Patent [19]

Devlin

[11] Patent Number: 4,555,260

[45] Date of Patent: Nov. 26, 1985

[54] METHOD FOR STERILIZING MALE PARTS OF PLANTS

[75] Inventor: Barry R. J. Devlin, Sittingbourne, England

[73] Assignee: Shell Oil Company, Houston, Tex.

[21] Appl. No.: 523,227

[22] Filed: Aug. 15, 1983

Related U.S. Application Data

[63] Continuation-in-part of Ser. No. 395,401, Jul. 6, 1982, abandoned, and a continuation of Ser. No. 289,552, Aug. 3, 1981, abandoned, and a continuation of Ser. No. 201,107, Oct. 28, 1980, abandoned, and a continuation-in-part of Ser. No. 395,525, Jul. 6, 1982, abandoned, which is a continuation-in-part of Ser. No. 289,552.

[30] Foreign Application Priority Data

Nov. 16, 1979 [GB] United Kingdom ................. 7939781

[51] Int. Cl.$^4$ ............................................. A01N 43/00
[52] U.S. Cl. ........................................................ 71/88
[58] Field of Search ........................................... 71/88

[56] References Cited

U.S. PATENT DOCUMENTS 4,047,930  9/1977  Kerr ........................................ 71/76

OTHER PUBLICATIONS

Anderson, Jr. et al., "The Synthesis of, etc.," (1972), J. Org. Chem., vol. 37, No. 24, pp. 3953–3955, (1972).
Britikov et al., "Effect of Proline, etc.," (1966), Fisiol. Rast. 13, No. 6, pp. 1–18, (Eng. trans.).

*Primary Examiner*—Glennon H. Hollrah
*Assistant Examiner*—Andrew Duff Meikle

[57] ABSTRACT

3-Carboxyazetidine or a hydrate, salt or lower alkyl ester thereof is used to sterilize male parts of plants.

9 Claims, No Drawings

METHOD FOR STERILIZING MALE PARTS OF PLANTS

This application is a continuation-in-part of application Ser. No. 395,401, filed July 6, 1982, abandoned, a continuation of application Ser. No. 289,552, filed on Aug. 3, 1981, abandoned, a continuation of application Ser. No. 201,107, filed on Oct. 28, 1980, abandoned. This application also is a continuation-in-part of application Ser. No. 395,525, filed July 6, 1982, abandoned, a continuation-in-part of application Ser. No. 289,552.

BACKGROUND OF THE INVENTION

To obtain $F_1$ hybrid seeds, which have many advantages over non-hybrid seeds, seed breeders cross-pollinate carefully selected parent plants. In the case of plants, for example small grain cereal plants, which have hermaphroditic flowers and normally self-pollinate, this is achieved by removing the male anthers from each of the flowers by hand, an operation which is extremely time consuming and requires highly-skilled workers. Much research is being carried out into treatments with chemicals by which this same result can be achieved without the necessity for such hand-operations.

DESCRIPTION OF THE INVENTION

It has now been found that 3-carboxyazetidine, its hydrates, salts and lower alkyl esters, sterilize the male parts of plants, by way of rendering the pollen grans nonfunctional—i.e., sterile. The present invention thus provides a method of sterilizing the male parts of a plant, which comprises applying to a plant an effective amount of 3-carboxyazetidine, of the formula

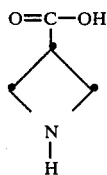

(I)

or a hydrate, lower alkyl ester, or salt thereof.

Suitable salts include, for example, the hydrohalide and alkali metal salts of the acid. Of the esters, it appears that the methyl and ethyl esters are more effective and therefore are to be preferred.

The method according to the invention generally produces plants in which male sterility has been introduced without an unduly adverse effect upon the female fertility of the plants. The treated plants thus are quite suitable for use in hybrid seed production. Also, the method of the invention can be used in cases where no fruit set is desirable—for example, in cases where a plant is to be used for ornamental foliage only, and it is desirable to avoid the mess caused by unwanted fallen fruit.

Although the method of the invention is particularly adapted to treatment of cereal grain plants, it is adapted to treatment of flowering plants, generally. The method thus is of interest with respect to the breeding of such crop plants as wheat, barley, oats, rye, flax, hops, maize, sorghum, buckwheat, millet, triticale, sesame, soybeans, rapeseed, sunflowers, safflower, lentils, mustard, cotton, peanuts, rice, sugarbeets, sugarcane and tobacco; vegetables such as tomatoes, beans, peas, celery and onions; grassy and broadleaved forage crops, such as alfalfa, clover, Sudan grass, lespedeza, vetch and grasses; cucurbits such as cucumbers, squash and melons; crucifers (cole crops) such as cabbage, broccoli and cauliflower; and ornamental plants such as annual and perennial plants of interest in the nursery or home garden trades. The method of the invention also can be used in effecting wide crosses, between different species of plants, where such is possible genetically—as in cross-breeding of different species of cultivated plants, cross-breeding of different species of cultivated and wild plants, and cross-breeding of crop plants with their wild relatives.

It appears that the azetidine has the desired effect when it is applied to the plant at a time during the development of the pollen—i.e., between the time of floral initiation and pollen shed. Preferably, the azetidine is applied somewhat before the pollen is wholly mature, to ensure movement of an effective dosage of the azetidine into the concerned plant tissue, believed to be the pollen grains, in time to effect sterilization of the pollen. For illustration, in the case of small-grain cereal plants, such as wheat and barley, this "application window" appears to extend from about growth stage 32 (second stem node detectable; anthers beginning to differentiate) to about growth stage 49 (awns appearing—i.e., late booting; pollen grains well developed). The definitions and meanings of the numbered growth stages are those set out by D. R. Tottman and R. J. Makepeace, Annals of Applied Biology, 93, 221-234 (1979).

The azetidine is suitably applied at a dosage of from 0.05 to 5 kilograms/hectare, preferably 0.10 to 2.0 kilograms/hectare.

The azetidine is systemic—that is, when applied to the foliage or roots of a plant, it penetrates into, and disseminates throughout, the tissues of the plant. The azetidine is not significantly toxic to plants at the dosages required to sterilize the pollen therein.

The present invention also provides a method of producing $F_1$ hybrid seed, which includes cross-pollinating a plant which has been treated by a process according to the invention with a second untreated plant of a different variety or strain.

The azetidine ordinarily will be formulated for use in the method of the invention. The invention, therefore, also provides a pollen-sterilizing composition which comprises 3-carboxyazetidine, or a hydrate, lower alkyl ester or salt thereof, together with a suitable carrier.

A carrier in a composition according to the invention is any inert material with which the active ingredient is formulated to facilitate application to the plant to be treated, or to facilitate storage, transport or handling. A carrier may be a solid or a liquid, including a material which is normally gaseous but which has been compressed to form a liquid, and any of the carriers normally used in formulating agricultural compositions may be used.

Suitable solid carriers include natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements, for example, carbon and sulfur; natural and synthetic resins, for example, coumarone resins, polyvinyl chloride, and styrene polymers and copolymers.

Suitable liquid carriers include water; alcohols, for example, isopropanol and glycols; ketones, for example, acetone, methyl ethyl ketone, methyl isobutyl ketone and cyclohexanone; ethers; aromatic or araliphatic hydrocarbons, for example, benzene, toluene and xylene; petroleum fractions, for example, kerosene and light mineral oils. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus, preferably, at least one carrier in a composition according to the invention is a surface-active agent. For example, the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulfonic acids; the condensation products of fatty acids or aliphatic amines or amides containing at least 9 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohol or alkyl phenols, for example, p-octylphenol or p-octylcresol, with ethylene oxide and/or propylene oxide; sulfates or sulfonates of these condensation products; alkali or alkaline earth metal salts, preferably sodium salts, of sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxide.

The compositions of the invention may, for example, be formulated as soluble or wettable powders, solutions, emulsifiable concentrates, emulsions, suspension concentrates and aerosols. Wettable powders usually contain 25, 50 and 75%w of active ingredient and usually contain, in addition to solid inert carrier, 3–10%w of a dispersing agent and, where necessary, 0–10%w of stabilizer(s) and/or other additives such as penetrates or stickers. Emulsifiable concentrates usually contain, in addition to a solvent and, when necessary, co-solvent, 10–50% w/v active ingredient, 2–20% w/v emulsifiers and 0–20% w/v of other additives such as stabilizers, penetrants and corrosion inhibitors.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick "mayonnaise"-like consistency.

In many, if not most, cases, the azetidine is conveniently applied as a water solution containing a small amount of an inert surfactant, a nonionic material being suitable for the purpose. The surfactant of course must be a material that is not toxic to the plant to be treated, at the dosage of the azetidine which is to be used.

The following Examples illustrated the invention. In each case, the identity of each product was confirmed by appropriate chemical and spectral analyses.

EXAMPLE 1

Preparation of 3-carboxyazetidine (1) (By the method of A. G. Anderson, Jr. and R. Lok, J. Org. Chem., 37, 3953–5 (1972))

(a) 15 g of 1-diphenylmethyl-3-cyanoazetidine (Anderson and Lok) was mixed with 150 ml of 2-methoxyethanol and added to a solution of 13 g of potassium hydroxide in 10 ml of water. The resulting mixture was refluxed for 15 hours, during which time ammonia was evolved, and then poured onto 1500 ml of ice and water. This mixture was then acidified with dilute hydrochloric acid until the pH was 1.5, and was then extracted with dichloromethane. The aqueous phase was adjusted to pH 5 by addition of solid sodium bicarbonate to the stirred solution. 1-diphenylmethyl-3-carboxyazetidine (1A) separated from the solution as a fine white solid. The solid was collected, washed with water and air-dried. M.p.: 190°–191° C. with decomposition.

(b) 10 g of 1A was suspended in 300 ml of methanol, and 6 g of a catalyst of palladium II hydroxide on charcoal, prepared by the method described in Tetrahedron Letters, 1967, page 1663, was added. The mixture was hydrogenated in a Parr apparatus at an initial hydrogen pressure of about 3.5 atmospheres absolute for 3 hours. Uptake of hydrogen stopped abruptly after 1 hour. The solution was filtered and evaporated almost to dryness under reduced pressure. The aqueous residue was extracted several times with dichloromethane and the combined extract phase was evaporated to dryness. The white solid residue was recrystallized from ethanol to give shiny plates of hydrated 1, m.p.: 169°–170° C. with decomposition.

Evaporation of the recrystallizing solvent gave a further crop of crystals, melting point 235°–270° C. with decomposition. These crystals consisted of anhydrous 1, and had an NMR spectrum identical to the hydrated acid.

EXAMPLE 2

Preparation of 3-carboxyazetidine methyl ester hydrochloride (2)

15.0 g of thionyl chloride was added over 30 minutes to a stirred solution of 5.06 g of 1 in 200 ml of dry methanol at 0°–5° C.

The resulting solution was stirred for 15 hours at room temperature, then was stripped under reduced pressure (<1 Torr.) for several hours to give 2, as a colorless solid, m.p.: 86°–90° C.

EXAMPLE 3

3-carboxyazetidine ethyl ester hydrochloride (3) was prepared as a pale yellow solid, m.p.: 50°–58° C., from ethanol by the procedures described in Example 2.

EXAMPLE 4

Demonstration of pollen-sterilizing activity

Spring wheat, variety Sicco, was propagated in a glasshouse in 13 centimeter pots containing a loam-based compost. Supplementary lighting was provided by high-pressure mercury vapor lamps to give a constant day length of 16 hours. The temperature was maintained at approximately 20° C.

The compound to be tested was formulated as an aqueous solution containing 0.1% Nonidet P 40 (trade mark) as wetting agent and 1% acetone to aid solubility. This formulation was diluted with water to a concentration of 1000 parts per million, and sprayed onto plants to runoff. The plants were treated at the growth stage when the second node of the plant was just detectable.

At ear emergence but before anthesis, 5 heads from each treated pot were placed in cellophane bags to prevent cross-pollination. At maturity, the bagged ears were harvested, and seed set was recorded and compared with untreated controls.

The results are shown in the following table.

| Compound No. | Grain Set Inhibition (% of control) |
|---|---|
| 1 | 87 |

It can be seen that the test compound produced a considerable reduction in seed set compared with the untreated control, clearly illustrating the ability of the compounds to sterilize the male parts of the wheat.

EXAMPLE 5

Limited-scale field tests conducted in England confirmed the effect of Compound 1 shown in Example 4. Twenty-three different winter wheat cultivars were employed. In those tests, several different dosages of Compound 1 (as a water solution containing 0.5% v/v Tween 20 as wetting agent) were sprayed on groups of plants, each group being at a different stage of growth (from about growth stage 31 to about growth stage 41 (Tottman and Makepeace)).

With the exception of a few cases wherein it appeared that rain had washed off the compound before an effective dosage had passed into the plant, grain set inhibition (i.e., sterilization of the pollen) was noted, the degree of inhibition varying from case to case, depending upon the cultivar involved, the dosage of the compound, and the stage of growth of the plants when the compound was applied. At the optimum dosage of Compound 1 (1.6 kg/hectare) and growth stage (about growth stage 37), grain set inhibition with respect to most of the cultivars was 95% or greater compared with the control plants. No significant phytotoxicity or other adverse growth effect was noted. Slight transient chlorosis was seen in some cases, and flag leaf development was slightly delayed in some cases.

EXAMPLE 6

Limited-scale field tests conducted in the United States also confirmed the effect of Compound 1.

Four conventional hard red spring wheat cultivars and lines were employed. A pollinator cultivar was planted in alternate strips in the test area. The plants were treated at growth stage 34, at two rates: 800 and 1230 grams of Compound 1 per hectare. The compound was applied as a water solution containing 0.4% w/v of Tween 20 as wetting agent/spreader, at the rate of 1000 liters per hectare.

Near complete (more than 98%) male sterility was induced by Compound 1 in three of the cultivars at both dosages. In the case of the other cultivar, inhibition of seed set in unpollinated ears was about 91% at the low dosage and about 97% at the high dosage.

At most, only very slight phytotoxic effects were noted.

EXAMPLE 7

The effect of Compound 1 on barley was examined, using the general procedure and formulation described in Example 4. Compound 1 was applied at a dosage of 1400 grams/hectare to the plants at growth stage 39 (spike primordia length: 2.8–3.5 cm). Seed set in the bagged spikes was 1.2%, indicating essentially complete sterilization of the pollen.

EXAMPLE 8

A water solution of Compound 1 containing 1% Tween 20 (trade mark) as wetting agent was sprayed upon several maize plants, to provide between 15 and 60 milligrams of Compound 1 per plant. Growth stages at treatment ranged from 4.5 cm tassel spike length to tassel emergence (tassel length 10 to 15 cm). Untreated female plants were cross-pollinated using pollen from the treated plants. Comparison with control plants indicated that the treatment with Compound 1 had resulted in an average 87% sterilization of the pollen in the treated plants.

EXAMPLE 9

Tests using tomato plants show that treatments of plants with a water solution of Compound 1 containing 0.75% Tween 20 as wetting agent at 1 to 5 mg per plant when flower buds are visible results in an average of greater than 90% reduction in fruit or seed formation.

EXAMPLE 10

Preliminary tests with sunflower show that treatments with Compound 1 at 10 to 25 mg per plant 7–14 days prior to anthesis results in an average of 75% reduction in seed set of covered sunflower heads.

EXAMPLE 11

The capability of wheat plants to set seed by cross-pollination, following treatment of the plants with Compound 1, was assessed as follows:

Plants of spring wheat (*Triticum aestivum* cv. Yecora rojo) were grown in pots in a greenhouse under controlled conditions. The compound was applied as an aqueous solution containing 0.75% Tween 20 as surfactant, at the rate of 600 liters per hectare. Control plants were sprayed with water containing 0.75% Tween 20. The compound was applied at dosages of 62.5, 125, 250 and 500 grams per hectare, and was applied to the plants during spike development prior to head emergence. The stage of development (length of spike primordia) was determined by measuring the lengths of a random sample of five spikes. All were in the range of two to four centimeters in length (stages 33–43, Zadok's scale).

Following treatment, the plants were placed in a randomized block arrangement, with at least four replicates per treatment.

As the spikes emerged, the mainstem and first tiller of each plant were bagged to prevent cross-pollination. In some cases, half of the mainstem spikes per pot were hand-crossed with pollen from untreated plants. Control spikes were hand-crossed and a hand-emasculated control was included.

When the developing seeds reached the soft dough stage, water was withheld, to dry the seeds for harvest, and the number of seeds that had been set were counted. The following results were obtained.

TABLE 1

| Compound | Dosage (g/ha) | Seed set, treated heads[a] | Seed set, hand-crossed heads[a] |
|---|---|---|---|
| 1 | 62.5 | 17.6 ± 1.7 | 31.2 ± 1.8 |
|   | 125  | 2.4 ± 0.6  | 26.8 ± 1.6 |
|   | 250  | 0          | 24.2 ± 1.0 |
|   | 500  | 0          | 22.0 ± 1.3 |
| Hand-emasculated control | — | 27.9 ± 4.4 | 20.0 ± 0.8 |
| Control | — | 29.2 ± 2.2 | 31.3 ± 1.3 |

[a]Average seed set per bagged head, mainstem plus tiller heads ± standard error.

EXAMPLE 12

Compounds 2 and 3 were assessed by the procedures described in Example 11 to ascertain their effectiveness as pollen sterilants. They were applied at dosages of 1000 and 2000 grams per hectare. The following results were obtained.

TABLE II

| Compound | Dosage (g/ha) | Seed set, treated heads[a] Mainstem | Tiller |
|---|---|---|---|
| 2 | 1000 | 0 | 0 |
|   | 2000 | 0 | 0 |
| 3 | 1000 | 1.0 ± 0.5 | 0.7 ± 0.4 |
|   | 2000 | 0 | 2.4 ± 2.4 |
| Hand-emasculated control | — | 23.4 ± 0.7 | 16.9 ± 1.2 |

[a]Average seed set per bagged head ± standard error.

I claim:

1. A method for producing male sterility in a cereal grain plant without substantial effect on the female fertility of the plant, which comprises applying to the plant an effective dosage of 3-carboxyazetidine, a hydrate or salt thereof.

2. A method according to claim 1 wherein the azetidine is 3-carboxyazetidine.

3. A method for producing a hybrid seed which comprises applying to a candidate parent cereal grain plant a male-sterilizing effective dosage of 3-carboxyazetidine, a hydrate or salt thereof, thereafter causing the candidate plant to be pollinated with pollen from a candidate male parent plant, allowing the pollinated parent to mature until the seed is mature, and harvesting the seed.

4. A method according to claim 3 wherein the azetidine is 3-carboxyazetidine.

5. A method according to claim 2 wherein the plant is a wheat plant.

6. A method according to claim 2 wherein the plant is a barley plant.

7. A method according to claim 4 wherein the plant is a wheat plant.

8. A method according to claim 4 wherein the plant is a barley plant.

9. A method according to claim 1 wherein the 3-carboxyazetidine is a hydrohalide or alkali metal salt of 3-carboxyazetidine.

* * * * *